(12) United States Patent
Eisenkraetzer et al.

(10) Patent No.: US 7,374,333 B2
(45) Date of Patent: May 20, 2008

(54) AGITATOR

(75) Inventors: Detlef Eisenkraetzer, Iffeldorf (DE); Andreas Haug, Penzberg (DE)

(73) Assignee: Hoffmann-La Roche Inc., Nutley, NJ (US)

( * ) Notice: Subject to any disclaimer, the term of this patent is extended or adjusted under 35 U.S.C. 154(b) by 270 days.

(21) Appl. No.: 11/110,413

(22) Filed: Apr. 20, 2005

(65) Prior Publication Data

US 2005/0243646 A1  Nov. 3, 2005

(30) Foreign Application Priority Data

Apr. 22, 2004 (EP) .................... 04009501

(51) Int. Cl.
 *B01F 7/20* (2006.01)
 *B01F 15/00* (2006.01)
(52) U.S. Cl. .................... 366/330.3
(58) Field of Classification Search .......... 366/330.3
 See application file for complete search history.

(56) References Cited

U.S. PATENT DOCUMENTS

| 3,880,407 A | 4/1975 | List |
| 4,039,024 A | 8/1977 | List |
| 4,468,130 A | 8/1984 | Weetman |
| 4,896,971 A | 1/1990 | Weetman et al. |
| 5,052,892 A | 10/1991 | Fasano |
| 5,297,938 A | 3/1994 | Von Essen et al. |
| 5,316,443 A | 5/1994 | Smith |
| 5,326,226 A | 7/1994 | Wyczalkowski et al. |
| 5,791,780 A | 8/1998 | Bakker |
| 5,795,732 A | 8/1998 | Schilling et al. |
| 5,813,837 A * | 9/1998 | Yamamoto et al. ...... 416/223 R |

FOREIGN PATENT DOCUMENTS

| DE | 23 49 106 | 5/1974 |
| DE | 23 51 763 | 6/1974 |
| DE | 94 00 938 U | 6/1995 |
| EP | 0 745 666 | 12/1996 |
| EP | 1 588 758 | * 10/2005 |
| FR | 1600744 | * 7/1970 |
| FR | 1 600 744 | 9/1970 |
| JP | 2002/273188 | 9/2002 |
| WO | WO85/02131 | 5/1985 |
| WO | WO91/11620 | 8/1991 |

* cited by examiner

*Primary Examiner*—Tony G. Soohoo
(74) *Attorney, Agent, or Firm*—George W. Johnston; John P. Parise; Karen J. Ghinculov

(57) ABSTRACT

An agitator for use on an agitator shaft having an axis of rotation. The agitator has a blade mount configured and dimensioned to receive the agitator shaft and being further configured and dimensioned so as to hold a plurality of agitator blades radially with respect to the axis of rotation. Each agitator blade has a plurality of segments, including an upper segment relative to the axis of rotation and a lower segment relative to the axis of rotation. The segments are inclined at an acute angle relative to the axis of rotation in the direction of rotation, wherein the acute angle changes continuously or stepwise from about 25° at the upper segment to about 65° at the lower segment.

11 Claims, 5 Drawing Sheets

AGITATOR

BACKGROUND OF THE INVENTION

1. Field

The invention relates to an agitator suitable for use in bioreactors.

2. Description

Agitators in bioreactors are essentially used to equalize temperature differences and differences of concentrations of various constituents. Agitators intensify the heat exchange between the thermostatting elements and the fermentation broth. Agitators also prevent the cells from sedimenting and thus being inhomogeneously distributed during the fermentation. Another task of agitators is to disperse the gas phase in the fermentation broth.

In biotechnology, various types of agitators are used. The most frequently used agitator is the disc agitator. A standard disc agitator is, for example, the Rushton turbine having six perpendicularly arranged blades. Such an agitator generates a flow radial to the agitator axis. Above and beneath such an agitator, flow vortices are formed, which result in a high dispersion effect. A second agitator is the inclined-blade agitator. This is an agitator where the angle of attack of the blades (with respect to the agitator axis) while changeable is usually 45°. The inclined-blade agitator has primarily an axial transport direction with a radial component and therefore, achieves a highly effective mixing. One disadvantage of disc agitators or inclined-blade agitators is that such agitators are easily flooded especially in the case of high gas load. As a result, the disc agitators are no longer able to disperse the exiting gas completely. A third type of agitator, the propeller agitator, is used in cell fermentation, but to a far lesser extent than standard disc agitators or inclined-blade agitators. The flow in a propeller agitator is directed axially.

Fundamentals of agitator technology in bioreactors are disclosed, for example, in Riet, van't, Tramper, J., Basic Bioreactor Design, Chapter 4: Kinetics, Marcel Dekker Inc., 1991; Tatterson, G. B., Fluid Mixing and Gas Dispersion in Agitated Tanks, McGraw-Hill, Inc., 1991; and Bailey, J. E. and Ollis, D. F., Biochemical Engineering Fundamentals, Second Edition, McGraw-Hill, Inc., 1986. In EP 0 745 666, a bioreactor is disclosed that is equipped with disc agitators. Disc agitators are also disclosed in DE 23 49 106 and DE 23 51 763.

U.S. Pat. No. 4,468,130 discloses an inclined-blade agitator having cambered agitator blades, the angle of which changes about 16° over the agitator blade. The angle at the tip of the agitator blade is between 16° and 32°. U.S. Pat. No. 4,896,971 discloses an inclined-blade agitator having twisted agitator blades, with twisting between 8° to 12°. The angle at the tip of the agitator blade is between 18° and 34°.

U.S. Pat. No. 5,052,892 discloses an agitator having agitator blades which are bent once at the center, with the angle between the two parts of the agitator blades being about 20° to 30°. U.S. Pat. No. 5,297,938 likewise discloses an agitator with bent agitator blades, and the angle between the two parts from 7.5° to 22.5°. U.S. Pat. No. 5,316,443 discloses an agitator having a hook-shaped cross section. U.S. Pat. No. 5,326,226 discloses an agitator having twisted agitator blades with the angle of the agitator blades between 25° and 45°.

U.S. Pat. No. 5,791,780 discloses an agitator in which the agitator blades have a semicircular or semi-elliptical cross section, while FR 1 600 744 discloses an agitator in which the agitator blades have a mainly triangular cross section. DE 94 00 938 U discloses an agitator in which the agitator blades have an inner main blade connected with an outer side blade.

SUMMARY OF THE INVENTION

An agitator for use on an agitator shaft having an axis of rotation. The agitator has a blade mount configured and dimensioned to receive the agitator shaft and being further configured and dimensioned so as to hold a plurality of agitator blades radially with respect to the axis of rotation. Each agitator blade has a plurality of segments, including an upper segment relative to the axis of rotation and a lower segment relative to the axis of rotation. The segments are inclined at an acute angle relative to the axis of rotation in the direction of rotation, wherein the acute angle changes continuously or stepwise from about 25° at the upper segment to about 65° at the lower segment.

DETAILED DESCRIPTION OF THE INVENTION

Figure 1:
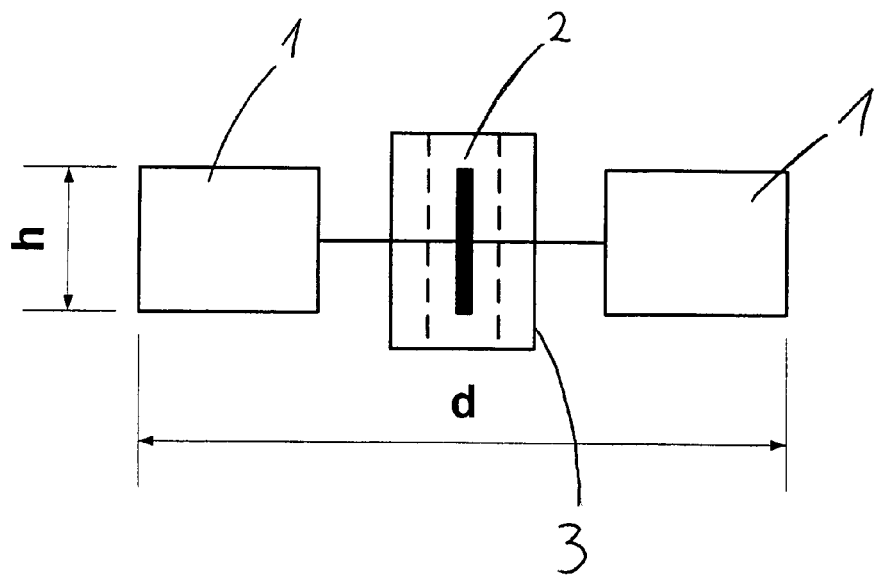
FIG. 1 Diagrammatic representation of a prior art agitator h: Agitator height (projected onto the vertical, see FIG. 2)

The subject invention will now be described in terms of its preferred embodiments. These embodiments are set forth to aid in understanding the invention, but are not to be construed as limiting.

The invention relates to an agitator for use in a bioreactor. The agitator has at least two agitator blades (1) that have segments with distal ends. The segments of the agitator blades are arranged radially to the axis of rotation (2) and inclined at an angle of attack in the direction of rotation relative to the axis of rotation (2). The angle of attack of the segments may change continuously or stepwise from 25° to 35° at the distal end of the upper segment to 55° to 65° at the distal end of the lower segment of the agitator blade. It is preferred that the angle of attack changes from 30° at the distal end of the upper segment to 60° at the distal end of the lower segment. The agitator may have two to eight agitator blades (1) on one plane, with four blades preferred. The agitator blades (1) may consist of several segments (5), and the angles of attack of each segment may be different. It is preferred that the angles of attack of the segments of an agitator blade be the same as the angles of attack for the segments of each additional agitator blade, although, as previously mentioned, the angle of attack of one segment of an agitator blade may be different than the angle of attack of a different segment of the same agitator blade. Depending on the size of the bioreactor, the agitator blades (1) can be arranged in a plurality of planes above and below one another. One to eight planes are expedient.

Preferably, the agitator blades (1) are fixed to a blade mount (3) which serves to receive the agitator shaft (4). If appropriate, the blade mount (3) is joined to the agitator shaft by fixing means. Such a blade mount (3) having agitator blades (1) fixed thereto is termed agitator element hereinafter. The agitator elements therefore preferably have a radially inner hollow ring region which encloses the agitator shaft (4), to which ring region two to eight agitator blades are attached at regular intervals from one another.

An agitator blade (1) may consist of equally large segments (5), with different angles of attack. The angle of attack of the distal end of the upper segment may be between 25° and 35°, and the angle of attack of the distal end of the lower segment may be between 55° and 65°. Preferably, an agitator blade (1) may consist of three equally large segments (5), with different angles of attack, where the angle of attack of the distal end of the upper segment is 30°; the angle of attack of the distal end of the middle segment is 45°; and the angle of attack of the distal end of the lower segment is 60°.

The agitator has a diameter equal to the diameter of a circle concentric to the axis of rotation and encircling the agitator blades. The ratio of the agitator diameter to the bioreactor internal diameter (in accordance with DIN 28131, the ratio d/D, agitator diameter/reactor internal diameter) of a single agitator blade may be in the range from 0.3 to 0.5, preferably from 0.35 to 0.45. Each agitator blade has a height, and the ratio of agitator blade height to agitator diameter (d/h) may be 0.1 to 0.3, and preferably 0.1 to 0.15 (see FIG. 1).

Dimensions of some agitators are set forth below:

| d/D | 0.33 | 0.4 |
|---|---|---|
| h/d | 0.14 | 0.2 |
| D | 350 mm | 350 mm |

The shape of an agitator blade may be rectangular, with the edges and corners rounded. The agitator blade could also have the shape of a cylindrical section or be bent once or several times to achieve the inventive angle of attack. The shape of the bioreactor is not critical. Usually, a cylindrical vessel is used.

Essential parameters for evaluating efficiency and performance of an agitator are the power input [W/m³], oxygen transport coefficient [$k_L a$ (1/h)], mixing time [S] and cell growth [cell concentration and vitality].

The oxygen transport coefficient $k_L a$ is determined according to the following formula:

$$k_L a = \frac{OTR}{(C^*_{O_2} - C_{O_2})}$$

$k_L a$: oxygen transfer coefficient
OTR: oxygen transfer rate [mol/(lh)]
$C^*_{O_2}$: equilibrium concentration of oxygen at the phase boundary
$C_{O_2}$: concentration of oxygen in the interior of the suspension [mol/l]

The $k_L a$ value can be determined by various methods. It has been found that the measurement range is method-dependent. In the present invention, the "dynamic method" was used to determine $k_L a$. Zlokarnik, M., Rührtechnik—Theorie und Praxis, Springer Verlag, Heidelberg, New York, 1999.

EXAMPLE 1

Fermenter:
A stirred-tank fermenter with a working volume of 10 l is used for culturing a CHO cell line. To produce the culture medium, the individual constituents are supplemented in heated purified water (type 2) in a sterile vessel. The media osmolality (0.29 Osmol/kg) is set, as in the experimental determination of the $k_L a$ value, by NaCl. The pH of 7.1 can be set via addition of correction agents.

The drive unit consists of a bench construction having a suspended electric drive motor. This is a 0.75 kW direct current motor having a range of speed of rotation of 0 to 1500 rpm. To form the supply unit, all apparatus, connections and fittings which are required for providing and removing steam, cooling water, wastewater, compressed air, carbon dioxide, nitrogen and correcting agents are combined. These include the heating system, gas mixing station and the pressure control valve. In addition, the electrical energy supply is included in the supply unit.

The bioreactor used has a height-to-diameter ratio (H/D) of 2.0. The reactor is constructed with dished base, flat lid and longitudinal inspection glass. The heating is performed via a jacketed heat exchanger (V=3L). In the vessel there are four baffles having a width of 0.1×D.

Three 25 mm and two 19 mm Ingold ports are let into the vessel wall laterally. Depending on the requirements of the measurement control instrumentation of the fermentation, a $pO_2$ electrode, a pH electrode, a temperature sensor (PT 100), a sampling valve (CV 25), a turbidity probe and $pCO_2$ electrode can be used.

Agitator Elements Used:
The agitator elements consist of stainless steel and are fixed via two grub screws on the agitator shaft which is centrally located in the fermenter. The direction of rotation was chosen to be anticlockwise. The number of agitator elements per fermenter was three for the standard disc agitator and two for the inclined-blade agitators.

Standard Disc Agitator (SSR):
The standard disc agitator consists of six fixed perpendicular discs symmetrically attached to a horizontally arranged disc (DIN 28 131). A standard disc agitator with a diameter ratio (D/d) of 0.4 was used.

Figure 2:
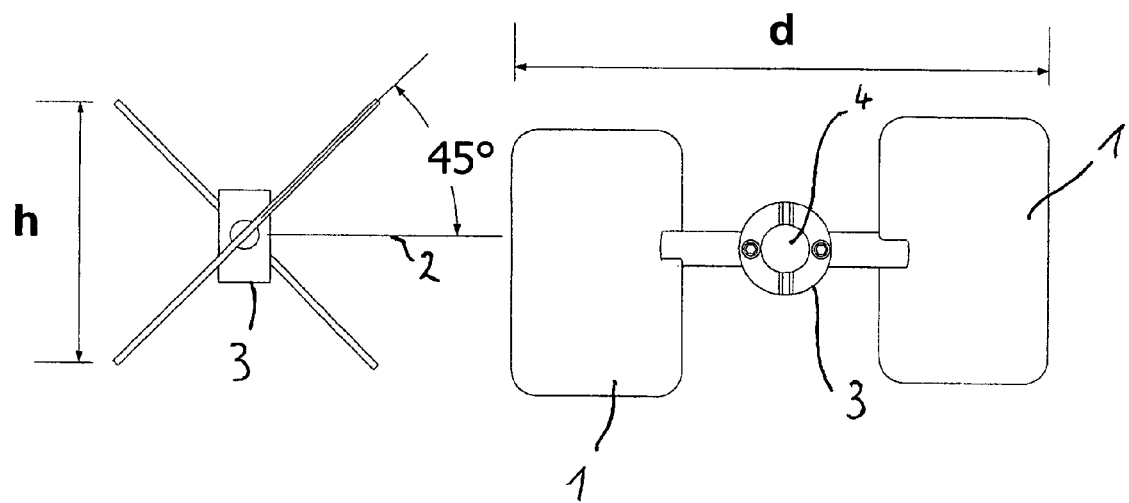
FIG. 2 Prior Art Inclined-blade agitator (SBR Type 1)

Inclined-Blade Agitator Type 1 (SBR Type 1) (FIG. 2):
The angle of attack of the paddles of the type 1 inclined-blade agitator was variable. The oxygen input was set for 45° (SBR Type 1) and for 60° (SBR Type 160°). The dimensions were as follows:

| d: | 118 cm |
|---|---|
| Blade width $d_B$: | 40 cm |
| Blade length: | 95 cm |
| Diameter ratio (d/D = 0.55) | |

Figure 3:
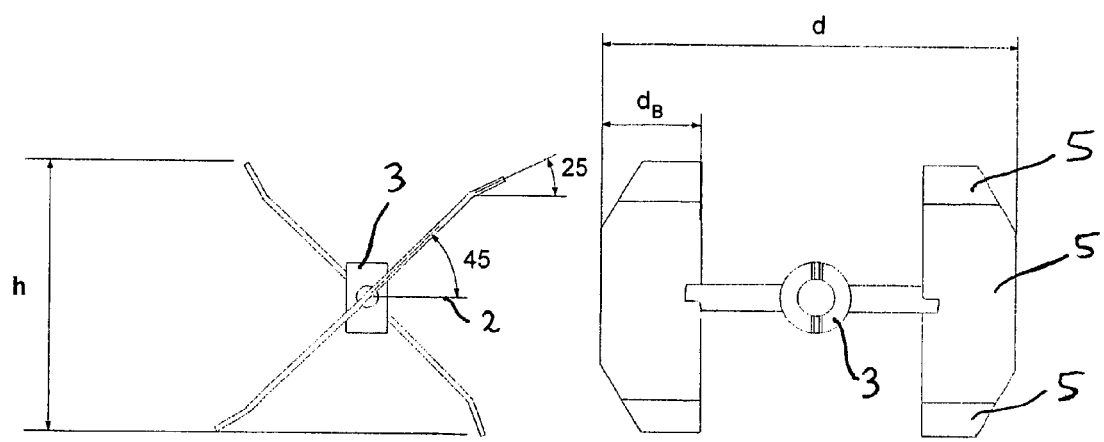
FIG. 3 Prior Art Inclined-blade agitator (SBR Type 2)

Inclined-Blade Agitator Type 2 (SBR Type 2) (FIG. 3):

In contrast to the type 1 inclined-blade agitator, the inclined-blade agitator type 2 was designed with a narrower but longer paddle surface. The paddle is slightly bent at the ends. The position of the bent ends is opposed (in Z shape).

The dimensions were as follows:

| | |
|---|---|
| d: | 118 cm |
| Blade width $d_B$: | 16/29 cm |
| Blade length: | 115 cm |
| Blade length without bent ends: | 93 cm |
| Diameter ratio (d/D = 0.55) | |

Figure 4:
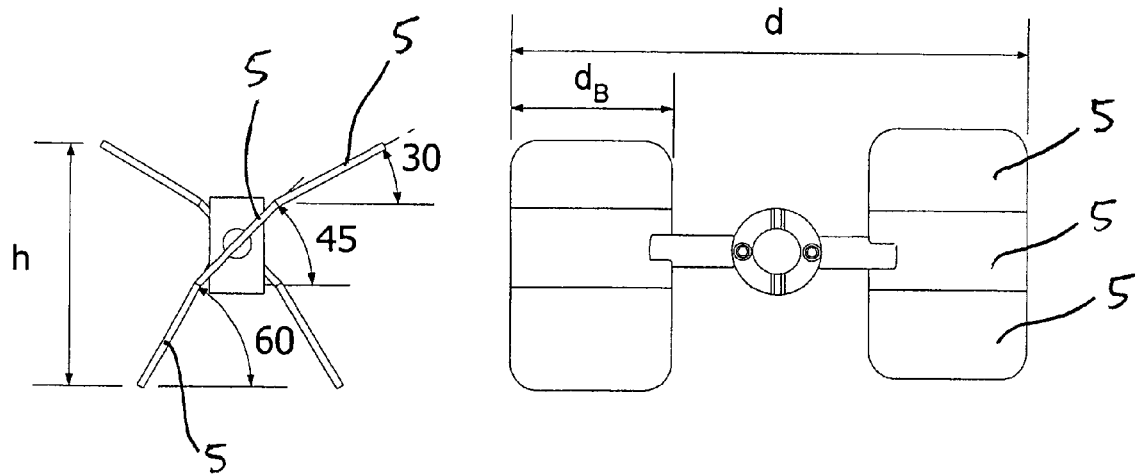
FIG. 4(a) Side view of the inventive agitator element (SBR Type 3)
FIG. 4(b) Top view of the inventive agitator element (SBR Type 3)
Figure 5:
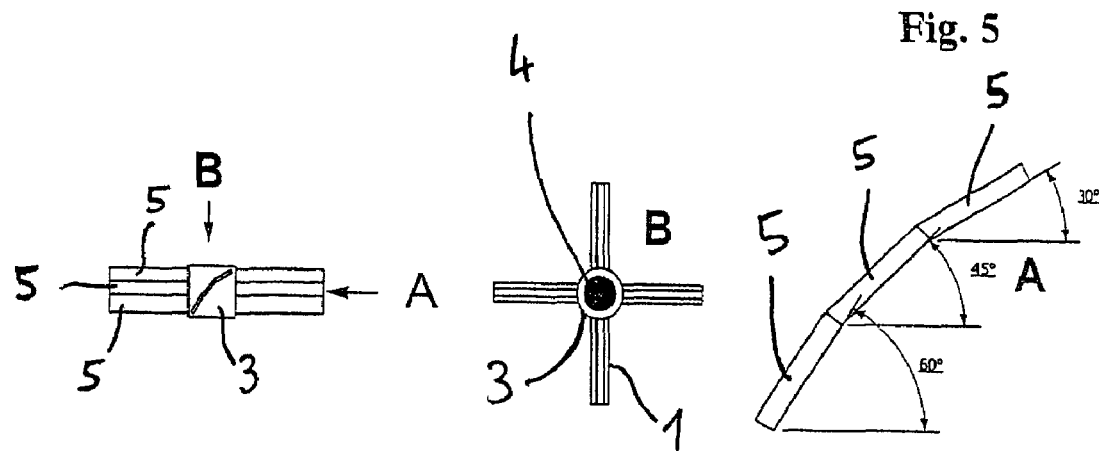
FIG. 5(a) Side view of the inventive agitator element
FIG. 5(b) Top view of four inventive agitator blades and the blade mount
FIG. 5(c) Side view of an inventive agitator blade

Inventive Inclined-Blade agitator (SBR Type 3) (FIGS. 4 and 5):

The inventive inclined-blade agitator SBR Type 3 is subdivided into three equal-sized segments. Each segment was 32 centimeters in length. In contrast to the inclined-blade agitator type 2, the outer segments were bent in the same direction (C shape). The two outer segments were inclined with respect to the central segment in the direction of rotation by 15°.

The dimensions were as follows:

| | |
|---|---|
| d/D: | 0.335 |
| d: | 350 mm |
| h/d: | 0.139 |

Measurement of Process Parameters:

Oxygen Measurements:

The dissolved oxygen concentration was determined using a Clark oxygen electrode (Metler Toledo, InPro® 6000).

Temperature, Pressure and pH Measurement:

The pH and temperature were measured in the fermentation system by probes installed in the probe ring. For the temperature measurement, a PT 100 resistance thermometer was used. Its accuracy is tested during sterilization and at prescribed time intervals during fermentation by a contact thermometer (Type CS 20). The pH was determined by a combination pH electrode from Ingold. Before installation, this electrode was calibrated with buffer solutions of pH=4.01 and pH=7.0. For measuring pressure, a pressure paste electrode was used.

Turbidity Measurement:

To determine the mixing times, a turbidity measurement system from Aquasant Messtechnik AG (AS81 with AF44) was used.

Experimental Determination of $k_L a$ Value:

The oxygen transport coefficient was determined by the saturation method. The fermentation system is charged with 10 l of deionized water after installation of the gas-introduction and agitator element under test. All internals (probes, baffles and riser pipes) and process parameters (p=1 bar, T=37° C., osmolality=0.3 Osmol/kg) correspond to those in the fermentation. The osmolality is set and checked by means of NaCl. After heating and calibrating the $pO_2$ electrode, all of the dissolved oxygen can be removed from the medium by gas introduction with nitrogen (Gas1=0.5 l/min, speed of rotation=250 rpm).

At time point t=0, pure compressed air introduction starts and the respective speed of rotation is set. The dissolved oxygen concentration increases to the saturation concentration of approximately 6.6 g/l. After three experiments the $pO_2$ electrode was recalibrated, and during long use of the same medium, the osmolality was checked daily.

The $k_L a$ value was calculated via the equation $$k_L a = -\frac{\ln[1 - (c_{O_2,L}/c^*_{O_2,L})]}{t}$$

It was determined as a function of speed of rotation and the feed gas volumetric flow rate (Gas1). For these parameters, ranges and steps were chosen which correspond to those of the fermentation. The test liquid used in the experiments was 0.15 molar NaCl solution (8.7 g/l). This has hydrodynamic properties (coalescence behaviour, oxygen saturation concentration) similar to the medium.

Figure 6:
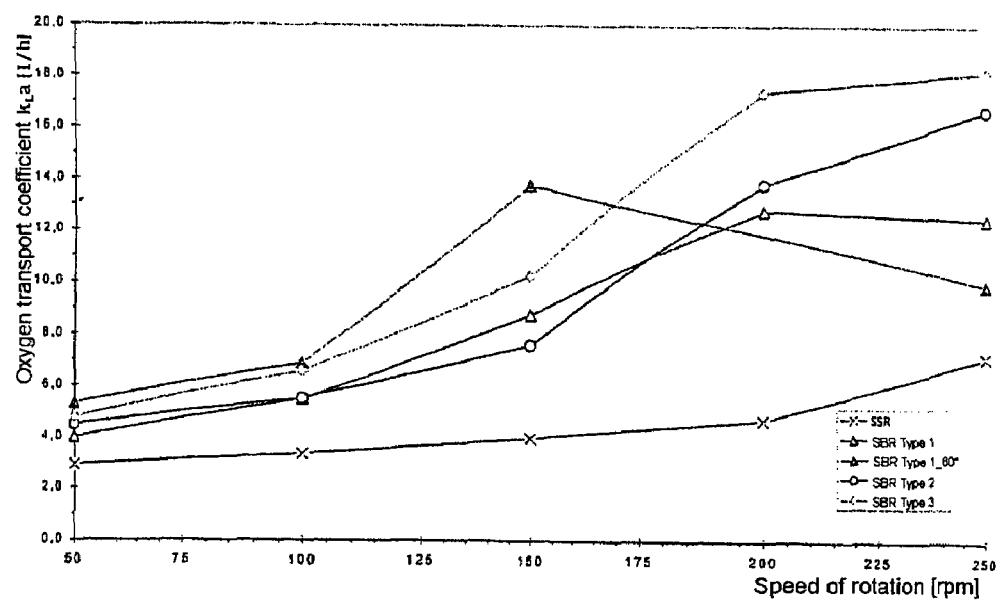
FIG. 6 Graph showing oxygen transport coefficient as a function of speed of rotation for SSR, SBR Type 1, SBR Type 160°, SBR Type 2, and SBR Type 3

By using the inventive inclined-blade agitator type 3, a markedly higher increase in $k_L a$ value could be achieved, compared with all other agitator systems used, not only with increasing speed of rotation but also with increasing gas-introduction rate. The fall in $k_L a$ value which occurs at a speed of rotation of 200 rpm when the inclined-blade agitator type 1 was used occurred in this agitator in the form of a reduced increase. The oxygen transport coefficients achieved by the standard disc agitator at 250 rpm could be achieved with the inclined-blade agitators at speeds of rotation of 100 to 150 rpm (FIG. 6).

Determination of Mixing Time:

The mixing time was measured using a turbidity measurement system with milk as tracer (all other conditions similar to the $k_L a$ value determination). At a tracer concentration of 5 ml/l, a measurement signal of 85% of the maximum measured value was established. The change in turbidity was followed by the turbidity probe installed in the probe ring and displayed on the compensation recorder. The termination condition for this experiment was a constant measurement signal of 85%. The time to achieve the desired mixing quality of 95% is the mixing time.

Figure 7:
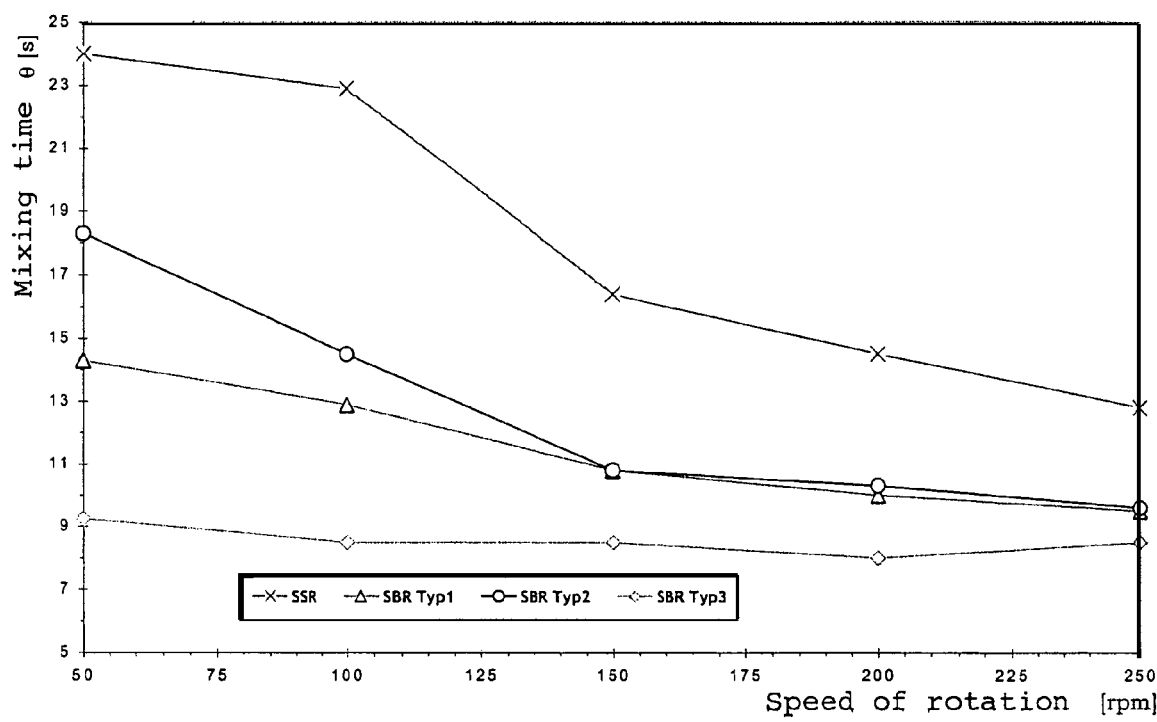
FIG. 7 Graph showing mixing time as a function of speed of rotation for SSR, SBR Type 1, SBR Type 2 and SBR Type 3

By using the inclined-blade agitator, the mixing times could be decreased by up to 70%. Using the inclined-blade agitator type 3, the mixing time could be decreased by approximately 40% compared with the other inclined-blade agitators (FIG. 7).

EXAMPLE 2

This experiment was performed analogous to the Example 1, but with a stirred-tank fermenter with a working volume of 1000 l. The fermenter was filled with a 0.15 mol NaCl water solution at 37° C.

Two different types of agitators were compared with respect to their oxygen transfer coefficient, $K_L a$, namely a standard inclined-blade agitator (SBR Type 1) and an inventive agitator (SBR Type 3). Before pure compressed air was introduced into the fermenter, oxygen was removed by the introduction of nitrogen (20 L/min, 150 rpm). Afterwards, pure air was introduced at different velocities (Gas 1=10, 12 or 20 L/min).

Figure 8:
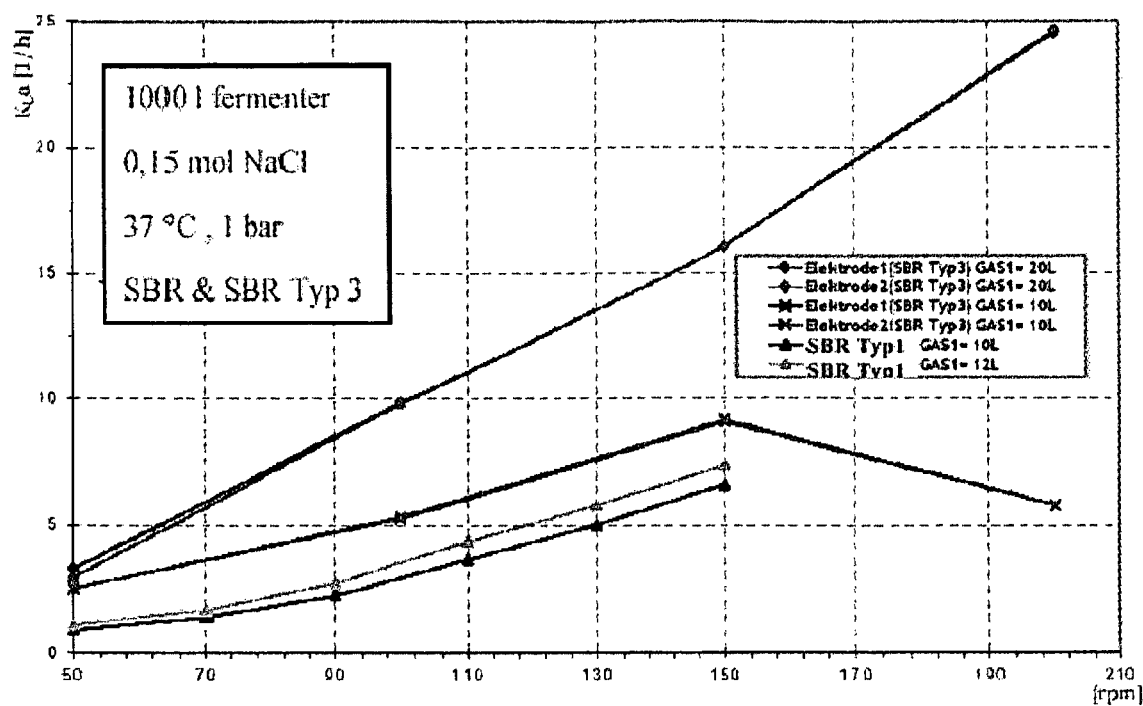
FIG. 8 Graph showing oxygen transport coefficient as a function of speed of rotation for a SBR Type 1 and a SBR Type 3 agitator in a 1000 L fermenter

The results of the experiment using two different oxygen electrodes (Electrode 1 and Electrode 2) are plotted as "oxygen transfer coefficient"-vs-"speed of rotation" in FIG. 8.

By using the inventive inclined-blade agitator type 3, the $k_L a$ value could be increased by a factor of between 1.5 and 2.7 compared with the standard agitator of type 1.

What is claimed is:

1. An agitator for use on an agitator shaft having an axis of rotation, which comprises:
   (a) a blade mount configured and dimensioned to receive the agitator shaft and being further configured and dimensioned so as to hold a plurality of agitator blades radially with respect to the axis of rotation, and
   (b) a plurality of agitator blades wherein each agitator blade has a plurality of segments, including an upper segment relative to the axis of rotation and a lower segment relative to the axis of rotation,
      (i) each segment is equally large and is inclined at an acute angle relative to the axis of rotation in the direction of rotation, and
      (ii) wherein the acute angle changes continuously or stepwise from about 25° at the upper segment to about 65° at the lower segment.

2. An agitator according to claim 1, wherein the acute angle changes continuously or stepwise from 25° to 35° at the upper segment to 55° to 65° at the lower segment.

3. An agitator according to claim 1, wherein the acute angle of the upper segment and the acute angle of the lower segment are complementary.

4. An agitator according to claim 1, wherein said blade mount further comprises means for fixing the agitator to the agitator shaft.

5. An agitator according to claim 1, wherein the plurality of segments includes an upper segment relative to the axis of rotation, a middle segment relative to the axis of rotation, and a lower segment relative to the axis of rotation.

6. An agitator according to claim 5, wherein said acute angle of the upper segment is about 25° to 35°, of the middle segment is about 40° to 50° and of the lower segment is about 55° to 65°.

7. An agitator according to claim 5, wherein said acute angle of the upper segment is about 25° to 35°, of the middle segment is about 45° and of the lower segment is about 55° to 65°.

8. An agitator according to claim 7, wherein said acute angle of the upper segment is 30°, of the middle segment is 45° and of the lower segment is 60°.

9. An agitator according to claim 1 for use in a bioreactor having an inner diameter which is concentric to the axis of rotation, wherein the agitator has a diameter equal to the smallest circle concentric to the axis of rotation that fully encircles the agitator blades and the ratio of the agitator diameter to the diameter of the bioreactor is 0.3 to 0.5.

10. An agitator according to claim 9, wherein the agitator blade has a height measured parallel to the axis of rotation equal to the distance from the end of the upper segment not in contact with another segment to the end of the lower segment not in contact with another segment, wherein the ratio of the height of the agitator to the agitator diameter is 0.1 to 0.3.

11. An agitator according to claim 1, wherein the agitator has two to eight agitator blades.

* * * * *